United States Patent [19]

Berney

[11] 4,282,251

[45] Aug. 4, 1981

[54] TRANS-N-CINNAMYL-N-METHYL-(1-NAPHTHYLMETHYL)AMINE

[75] Inventor: Daniel Berney, Lausanne, Switzerland

[73] Assignee: Sandoz Ltd., Basel, Switzerland

[21] Appl. No.: 100,024

[22] Filed: Dec. 3, 1979

Related U.S. Application Data

[63] Continuation-in-part of Ser. No. 1,479, Jan. 8, 1979, abandoned, which is a continuation of Ser. No. 789,808, Apr. 22, 1977, abandoned.

[30] Foreign Application Priority Data

Apr. 28, 1976 [CH] Switzerland ............... 5335/76
Dec. 22, 1976 [CH] Switzerland ............. 16182/76
Jan. 26, 1977 [CH] Switzerland ................ 920/77
Jan. 26, 1977 [CH] Switzerland ................ 921/77

[51] Int. Cl.$^3$ ............... A01N 33/02; A01N 37/30; C07C 87/28
[52] U.S. Cl. ................. 424/316; 260/501.1; 260/501.18; 260/501.19; 260/501.21; 424/330; 564/273; 564/274; 564/275; 564/363; 564/364; 564/365; 564/366; 564/383; 564/386; 564/387; 564/342; 564/343; 568/425; 568/426

[58] Field of Search ............. 260/570.8 R, 501.1, 260/501.18; 424/330, 316; 564/383, 387

[56] References Cited

U.S. PATENT DOCUMENTS

| 2,601,275 | 6/1952 | Gump et al. | 260/570.8 R |
|---|---|---|---|
| 2,609,392 | 9/1952 | Crossley | 260/570.8 X |
| 3,094,561 | 6/1963 | Faust et al. | 260/578.8 X |
| 3,366,688 | 1/1968 | Hargrove | 260/594 |
| 3,829,469 | 8/1974 | Thiele et al. | 260/570.8 X |

OTHER PUBLICATIONS

Biniecki et al. (I), "Chemical Abstracts", vol. 50, pp. 4096–4097 (1956).
Biniecki et al. (II), "Chemical Abstracts", vol. 49, p. 8153 (1955).
Gunn et al., "Chemical Abstracts", vol. 34, p. 8064.
Wagner et al., "Synthetic Organic Chemistry", pp. 666–669 (1953).

Primary Examiner—Robert V. Hines
Attorney, Agent, or Firm—Gerald D. Sharkin; Robert S. Honor; Thomas O. McGovern

[57] ABSTRACT

Cinnamylalkyl-1-naphthylmethylamines, useful as antimycotic agents, and processes for their production.

29 Claims, No Drawings

TRANS-N-CINNAMYL-N-METHYL-(1-NAPHTHYLMETHYL)AMINE

This application is a continuation-in-part of Ser. No. 01,479 filed Jan. 8, 1979 which in turn is a continuation of Ser. No. 789,808 filed Apr. 22, 1977, and now both abandoned.

This invention provides compounds of formula I,

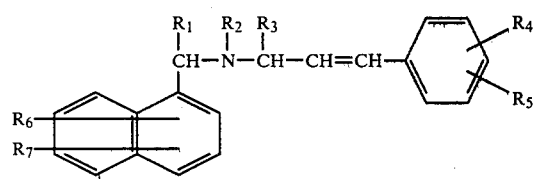

in which
$R_1$ is hydrogen or alkyl,
$R_2$ is alkyl, alkenyl, alkynyl, cycloalkyl or cycloalkylalkyl,
$R_3$ is hydrogen or lower alkyl, and
$R_4$, $R_5$, $R_6$ and $R_7$, which may be the same or different, each signifies hydrogen, halogen, trifluoromethyl, hydroxy, nitro or lower alkyl or alkoxy.

It will be appreciated that the compounds of formula I exist in the form of cis and trans isomers. It is to be understood that the invention embraces both isomeric forms and mixtures thereof.

In the compounds of formula I, $R_1$ may be hydrogen. It may also be alkyl, which can be straight or branched chain, in particular of 1 to 6, preferably 1 to 4 carbon atoms, more particularly methyl.

$R_2$ may be alkyl, which may be straight or branched chain, in particular of 1 to 6, preferably 1 to 4 carbon atoms, more particularly methyl. It may also be alkenyl, particularly of 3 to 6 carbon atoms, e.g. allyl. It may also be alkynyl of 3 to 6, preferably 3 or 4 carbon atoms. It may also be cycloalkyl, in particular of 3 to 6, preferably 5 or 6, ring carbon atoms. It may finally be cycloalkylalkyl. The cycloalkyl portion thereof suitably has 3 to 6, preferably 3 or 4, ring carbon atoms and the alkyl portion thereof suitably has 1 to 4, preferably 1 or 2, carbon atoms.

$R_3$ may be hydrogen. It may also be lower alkyl, preferably of 1 to 3 carbon atoms.

Any or all of $R_4$ to $R_7$ may signify (i) hydrogen; (ii) halogen; (iii) $CF_3$; (iv) OH; (v) $NO_2$; (vi) lower alkyl, preferably of 1 to 3 carbon atoms; or (vii) lower alkoxy, preferably of 1 to 3 carbon atoms.

As used herein, the term "halogen" means fluorine, chlorine or bromine, preferably (unless otherwise indicated) fluorine or chlorine.

The invention also provides processes for the production of compounds of formula I, characterised by (a) reacting a compound of formula II,

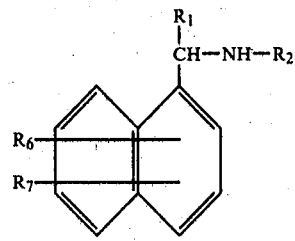

in which $R_1$, $R_2$, $R_6$ and $R_7$ are as defined above, with a compound of formula III,

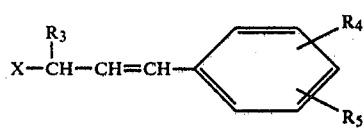

in which $R_3$, $R_4$ and $R_5$ are as defined above and X is a leaving group, (b) introducing the group $R_2$ into a compound of formula IV,

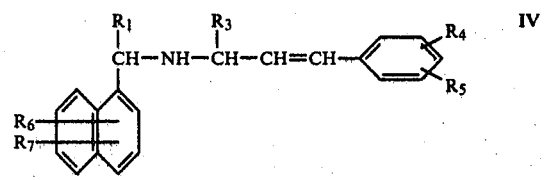

in which $R_1$, $R_3$, $R_4$, $R_5$, $R_6$ and $R_7$ are as defined above, (c) producing a compound of formula Ia,

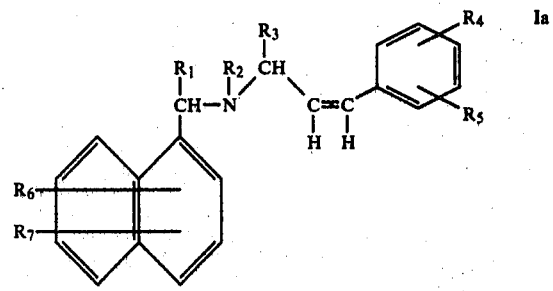

in which $R_1$ to $R_7$ are as defined above, by hydrogenating a compound of formula V,

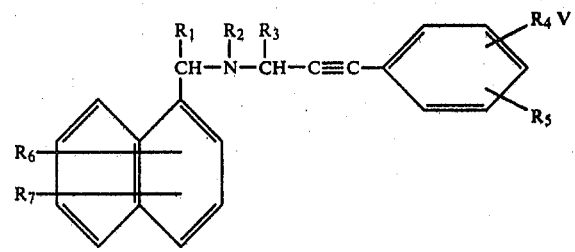

in which $R_1$ to $R_7$ are as defined above, or
(d) producing a compound of formula Ib,

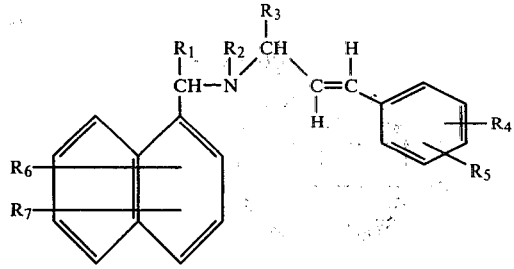

in which $R_1$ to $R_7$ are as defined above, by splitting off water from a compound of formula VI,

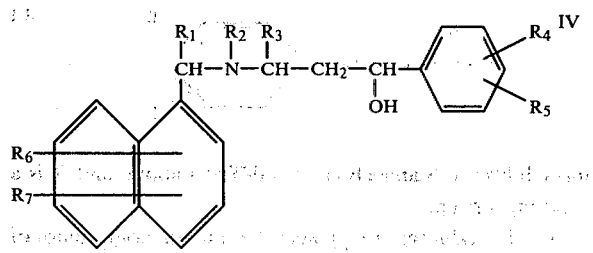

in which $R_1$ to $R_7$ are as defined above.

As indicated, process (c) leads to the products of the invention predominantly in cis isomeric form while process (d) leads to the products predominantly in trans isomeric form. The isomeric form of the products of processes (a) and (b) depends on the isomeric form of the starting material which can therefore be selected in accordance with desired form of the product.

Process (a) is suitably effected in an inert solvent, such as a lower alkanol, e.g. ethanol, optionally in aqueous admixture, an aromatic hydrocarbon, e.g. benzene or toluene, a cyclic ether, e.g. dioxane, or a carboxylic acid dialkylamide, e.g. dimethylformamide. The process may conveniently be carried out at a temperature of from room temperature to the boiling temperature of the reaction mixture, preferably at room temperature and is suitably effected in the presence of an acid binding agent, such as an alkali metal carbonate, e.g. sodium carbonate. The leaving group X in the compounds of formula III is suitably halogen, in particular chlorine or bromine, an organic sulphonyloxy group with 1 to 10 carbon atoms, e.g. $C_{1-10}$, preferably $C_{1-4}$, alkyl sulphonyloxy, in particular methylsulphonyloxy, or $C_{1-3}$-alkylphenylsulponyloxy, e.g. tosyloxy.

Process (b) may be effected in manner conventional for the "alkylation" (the term "alkylation" being used here to denote introduction of any of the hydrocarbyl groups $R_2$) of secondary amines, for example by direct "alkylation" with an "alkylating" agent, for example a halide or sulphate, or by reductive alkylation, in particular by reaction with an appropriate aldehyde and subsequent or simultaneous reduction. Reductive "alkylation" is suitably effected in an inert organic solvent, such as a lower alkanol, e.g. methanol, and at an elevated temperature, in particular at the boiling temperature of the reaction medium. The subsequent reduction may be effected with, for example, a complex metal hydride reducing agent, e.g. $NaBH_4$ or $LiAlH_4$. The reduction may also be effected simultaneously to the alkylation, for example by use of formic acid which may serve both as reducing agent and as a reaction medium.

Process (c) is conveniently effected in an inert solvent, e.g. a lower alkanol, such as methanol or ethanol, a chlorinated hydrocarbon, e.g. methylene chloride, pyridine or an ester, such as ethylacetate. The hydrogenation may be carried out in conventional manner, for example employing a catalyst, such as palladium or platinum, suitably on a carrier such as $BaSO_4$ or $CaCO_3$. The catalyst may also be partially inactivated, e.g. by pretreatment with lead salts (Lindlar catalysts).

Process (d) may suitably be carried out using a conventional dehydrating agent, e.g. an inorganic acid, such as hydrochloric acid or sulphuric acid, an organic acid, such as methane-, benzene- or p-toluenesulphonic acid, or anhydrides or halides thereof. The process may suitably be effected in an inert solvent although when an acid halide is employed as dehydrating agent, an excess thereof may be used to provide a reaction medium. An acid binding agent, e.g. a tertiary amine, such as trialkylamine or pyridine, is suitably present and the reaction temperature may, for example, range from $-10°$ to $+180°$ C. The process may also be effected using polyphosphoric acid. In this case, the reaction temperature is conveniently from $80°$ to $120°$ C. and an inert solvent, an inorganic acid, e.g. phosphoric acid or an organic acid, such as acetic acid, or an excess of the polyphosphoric acid, is suitably employed to provide a reaction medium.

The resulting compounds of formula I may be isolated and purified using conventional techniques. Where the process leads to mixtures of isomers, the individual isomers may be separated in conventional manner. Where required, free base forms thereof may be converted into acid addition salt forms in conventional manner, or vice versa.

The starting materials for use in the processes of the invention may, for example, be produced by the following reactions:

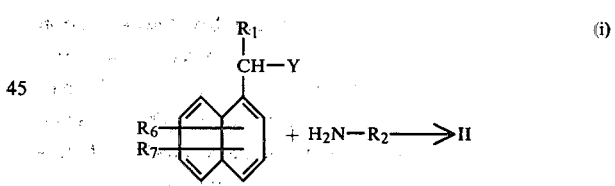

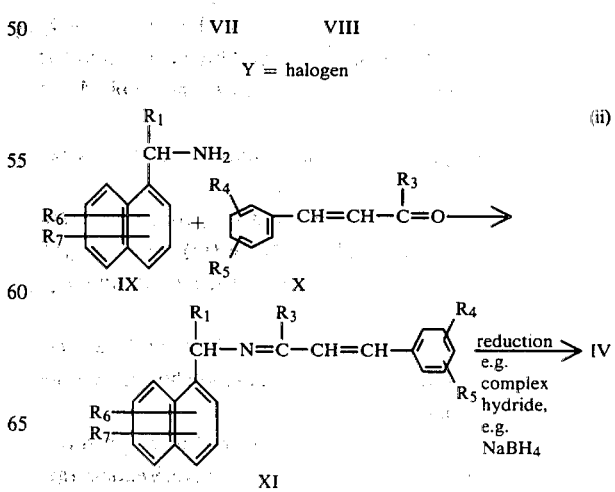

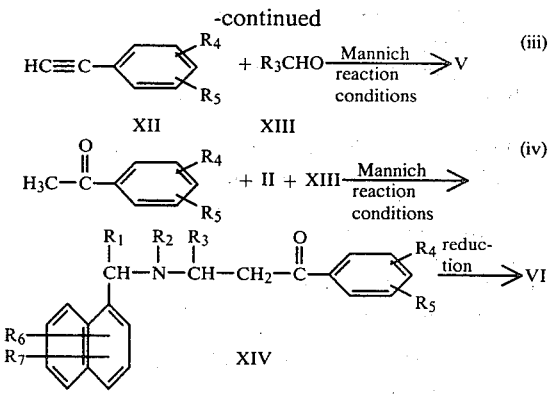

$R_1$ to $R_7$ in the above formulae being as defined above.

These processes may be carried out in conventional manner.

The starting materials of formulae III, VII, VIII, IX, X, XII, XIII and XV are either known or may be produced in conventional manner from available materials.

The compounds of formula I are useful because they possess chemotherapeutic activity. In particular, they are useful as antimycotic agents, as indicated in vitro in various families and types of mycetes, including dermatophytes such as *T. rubrum, T. mentagrophytes, T. mentagrophytes var. quinckeanum, E. floccosum, M. canis, M. gypseum* and *M. racemosum, Aspergillus fumigatus, Microsporum canis, Sporotrychius schenkii, Candida albicans* and *Candida parapsilosis,* at concentrations of, for example 0.1 to 100 μg/ml, and in vivo in the experimental skin mycosis model in guinea pigs. In this model, guinea pigs are infected by sub-cutaneous application of e.g. *Trichophyton quinkeanum.* The test substance is administered once daily for 7 days beginning 24 hours after the infection either by local application by rubbing the test substance (taken up in polyethylene glycol) on the skin surface, or perorally or sub-cutaneously, the test substance being administered as a suspension. The activity is shown on local application at concentrations of for example 0.1 to 5%, in particular 0.1 to 0.5%. The oral activity is shown at dosages of, for example, 50 to 100 mg/kg.

For the above-mentioned use, the dose administered will of course vary depending on the compound employed, mode of administration and treatment desired. However, in general, satisfactory results are obtained when administered at a daily dosage of from 10 to 100 mg/kg of animal body weight, conveniently given in divided doses two to four times daily, or in sustained release form. For the larger mammals, the corresponding daily dosages are in the range of from 500 to 2000 mg, and dosage forms suitable for oral administration comprise from 125 to 1000 mg.

The compounds may be used in free base form or in the form of chemotherapeutically acceptable acid addition salts; suitable acids for salt formation include inorganic acids, such as hydrochloric acid, and organic acids, such as naphthalene-1,5-disulphonic acid and fumaric acid (particularly to form the hydrogen fumarate).

The compounds may be admixed with conventional chemotherapeutically acceptable diluents and carriers, and, optionally, other excipients and administered in such forms as tablets or capsules. The compounds may alternatively be administered topically in such conventional forms as ointments or creams. The concentration of the active substance in such topical application forms will of course vary depending on the compound employed, the treatment desired and the nature of the form etc. In general, however, satisfactory results are obtained at concentrations of from 0.05 to 5, in particular 0.1 to 1 wt. %.

The preferred compounds of the invention are in trans form. A compound with particularly interesting activity is the compound of Example 1, hereinafter.

The following Examples illustrate the invention. All temperatures are in °C.

EXAMPLE 1

Trans-N-(cinnamylmethyl)-N-methyl-(1-naphthylmethyl)amine [Process a)]

To a mixture of 1.42 g of methyl-(1-naphthylmethyl)amine hydrochloride, 2.89 g of sodium carbonate and 10 ml of dimethyl formamide is added, at room temperature, 1.25 g of cinnamyl chloride, dropwise. After 18 hours stirring, at room temperature, the mixture is filtered and the filtrate is evaporated in vacuo. The residue is dissolved in toluene and, after drying over sodium sulphate, evaporated to obtain the heading compound, b.p. 162°–167° (0.015 Torr).

The free base may be converted, with isopropanolic hydrogen chloride solution, into the hydrochloride form, m.p. 177° C. (from propanol).

EXAMPLE 2

Trans-N-[3-(4-fluorophenyl)-2-propenyl]-N-methyl-(1-naphthylmethyl)amine [process b)]

(a) Trans-N-[3-(4-fluorophenyl)-2-propenyl]-(1-naphthylmethyl)amine

A mixture of 10 g of 1-aminomethylnaphthalene, 9.55 g of p-fluorocinnamaldehyde and 150 ml of benzene is heated in a reaction vessel equipped with a water separator, at reflux, until the theoretical amount of water has been separated. The mixture is cooled and evaporated to dryness. 5.78 g of the resulting Schiff's base in 60 ml of methanol, after warming to 50°, is mixed, with vigorous stirring, with 1.51 g of solid NaBH$_4$, portionwise, and the mixture is refluxed for 20 minutes. The resulting mixture may be used as such in the next stage. The title compound can be isolated as an oil, however, by evaporation and dividing the residue between aqueous NaHCO$_3$ solution and chloroform, drying the organic phase and evaporation.

(b) Trans-N-[3-(4-fluorophenyl)-2-propenyl]-N-methyl-(1-naphthylmethyl)amine [process b)]

(i) The reaction mixture resulting from step (a) is refluxed, after addition of 16 ml of 37% aqueous formaldehyde solution, for 1½ hours. The mixture is cooled and mixed, portionwise, in an ice bath and with vigorous stirring, with 7.6 g of NaBH$_4$. After 4 hours, the residue is centrifugally divided between aqueous NaHCO$_3$ solution and chloroform. The organic phase is dried and centrifuged to obtain the heading compound as an oil, m.p. hydrochloride form: 191°–206°.

(ii) The oil resulting from step (a) (2.9 g) is refluxed with 3.3 g of formic acid (98–100%) and 0.81 ml of 37% aqueous formaldehyde mixture is evaporated in vacuo, and the residue divided between chloroform and aqueous NaHCO$_3$ solution. The aqueous phase is washed with brine, dried and evaporated to obtain the heading compound, m.p. hydrochloride form: 191°–206°.

EXAMPLE 3

Cis-N-[3-(4-chlorophenyl)-2-propenyl]-N-methyl-1-naphthylmethyl)amine [process c)]

(a) N-[3-(4-Chlorophenyl)propargyl]-N-methyl-(1-naphthylmethyl)amine 15 g of methyl-(1-naphthylmethyl)amine, 12 g of p-chlorophenylacetylene, 2.61 g of paraformaldehyde and 1.1 g of zinc chloride are refluxed in absolute dioxane, in the absence of water, for 3 hours. The mixture is then evaporated and the residue is divided between saturated aqueous NaHCO$_3$ solution and chloroform. The organic phase is dried and evaporated and the crude product is recrystallised from ethanol, m.p. 74°–75°.

(b) Cis-N-[3-(4-chlorophenyl)-2-propenyl]-N-methyl-(1-naphthylmethyl)amine 3 g of [3-(4-chlorophenyl)propargyl]-methyl-(1-naphthylmethyl)amine are dissolved in 50 ml of absolute pyridine. The solution is hydrogenated employing 150 mg of Pd/BaSO$_4$ (5%) until the theoretical amount of hydrogen has been taken up. The catalyst is filtered off and the mixture evaporated. The oily residue is chromatographed over silica gel using benzene/ethyl acetate (9:1) as eluant, to obtain the pure heading compound, m.p. 41°–42° (from ethanol/water).

EXAMPLE 4

Trans-N-methyl-N-[3-(4-tolyl)-2-propenyl]-(1-naphthylmethyl)amine (a) N-Methyl-(1-naphthylmethyl)amine 17.6 g of 1-chloromethyl-naphthalene in 40 ml of absolute ethanol is added, dropwise, at 0° to 5°, to 100 ml of a 33% solution of methylamine in absolute ethanol. The mixture is allowed to stand overnight and is then evaporated. The residue is taken up in a little chloroform and washed with 100 ml of 1 N sodium hydroxide solution and with water. The organic phase is dried and evaporated to dryness. The residue is distilled at 0.01 Torr to obtain the heading compound as main fraction, b.p. 85°–87°.

(b) β-(N-methyl-(1-naphthylmethyl)amino]ethyl-(4-tolyl)ketone 17.1 g of methyl-(1-naphthylmethyl)amine are dissolved in 200 ml of methanol and 10 ml of concentrated hydrochloric acid, 13.4 g of 4-tolylmethylketone and 100 ml of 35% formaldehyde solution are sequentially added. The mixture is refluxed for 1½ hours, with stirring, cooled, diluted with 1 liter of water, made alkaline with 30% sodium hydroxide solution and exhaustively extracted with chloroform. The organic extract is dried and evaporated to dryness and the oily residue is dissolved in petroleum ether and allowed to crystallise in the cold, to obtain the heading compound, m.p. 92°–95°.

(c) 3-[N-methyl]-(1-naphthylmethyl)amino]-1-(4-tolyl)-propan-1-ol

To a solution of 7.5 g of β-[methyl-(1-naphthylmethyl)amino]ethyl-(4-tolyl)ketone in 400 ml of methanol is added, portionwise, at room temperature, 1 g of NaBH$_4$. The mixture is stirred for 15 minutes and the solvent is then evaporated off. The oily residue is taken up in chloroform and washed with water. The organic phase is dried and evaporated to dryness to obtain the crude heading product which is used as such in the next stage.

(d) Trans-N-methyl-N-[3-(4-tolyl)-2-propenyl]-(1-naphthylmethyl)-amine 8.4 g of 3-[methyl]-(1-naphthylmethyl)amino]-1-(4-tolyl)-propan-1-ol are refluxed, with stirring, in 300 ml of 5 N hydrochloric acid for 1½ hours. The mixture is isolated by addition of ice, made alkaline with 30% sodium hydroxide solution and exhaustively extracted with chloroform. The chloroform extract is dried over sodium sulphate, filtered and evaporated to dryness. The oily residue is dissolved in absolute ethanol and made acid with etheric hydrochloric acid. After addition of ether, the heading compound is obtained, m.p. 207°–211°.

In manner analogous to the Example indicated, and employing appropriate starting materials in approximately equivalent amounts, the compounds of formula I indicated in the following Table may be obtained.

| Ex. | R$_1$ | R$_2$ | R$_3$ | R$_4$ | R$_5$ | R$_6$ | R$_7$ | Analogous to Example | M.P. °C. | Centrifugation |
|---|---|---|---|---|---|---|---|---|---|---|
| 5 | H | CH$_3$ | H | 4-Cl | H | H | H | 1, 2 or 4 | 209–212[1] | Trans |
| 6 | H | CH$_3$ | H | 4-CH$_3$ | H | H | H | 1 or 2 | 207–211[1] | " |
| 7 | H | CH$_3$ | H | 4-F | H | H | H | 1 or 4 | 191–206[1] | " |
| 8 | H | CH$_3$ | H | 4-Cl | 3-Cl | H | H | 1, 2 or 4 | 187–192[1] | " |
| 9 | H | CH$_3$ | H | 4-OCH$_3$ | H | H | H | 1, 2 or 4 | 193–196[1] | " |
| 10 | H | CH$_3$ | H | H | H | 2-OH | H | 1, 2 or 4 | 197–199[2] | " |
| 11 | H | CH(CH$_3$)$_2$ | H | H | H | H | H | 1, 2 or 4 | 225–230[2] | " |
| 12 | H | CH$_3$ | H | H | H | 2-CH$_3$ | H | 1, 2 or 4 | 204–208[1] | " |
| 13 | CH$_3$ | CH$_3$ | H | H | H | H | H | 1, 2 or 4 | 213–215[2] | " |
| 14 | H | CH$_3$ | H | 2-F | H | H | H | 1, 2 or 4 | 176–181[1] | " |
| 15 | H | CH$_3$ | H | 2-Cl | H | H | H | 1, 2 or 4 | 178–181[1] | " |
| 16 | H | CH$_3$ | H | 4-OH | H | H | H | 1, 2 or 4 | 196–200[2] | " |
| 17 | H | C$_2$H$_5$ | H | H | H | H | H | 1, 2 or 4 | 127–129[3] | " |
| 18 | H | CH$_3$ | H | H | H | 4-Cl | H | 1, 2 or 4 | 198–208[1] | " |
| 19 | H | CH$_3$ | H | H | H | 4-CH$_3$ | H | 1, 2 or 4 | 197–201[1] | " |
| 20 | H | CH$_3$ | H | H | H | 2-OCH$_3$ | H | 1, 2 or 4 | 248–250[2] | " |
| 21 | H | CH$_3$ | H | H | H | 4-OCH$_3$ | H | 1, 2 or 4 | 211–214[1] | " |
| 22 | H | CH$_3$ | H | H | H | H | H | 1, 2 or 3 | oil[4,5] | cis |
| 23 | H | CH$_3$ | H | 4-F | H | H | H | 1, 2 or 3 | oil[6,7] | " |
| 24 | H | CH$_3$ | H | 4-Cl | H | H | H | 1 or 2 | 41–42 | ' |
| 25 | H | CH$_2$—CH=CH$_2$ | H | H | H | H | H | 1, 2 or 4 | 95–103[1] | trans |
| 26 | H | CH$_3$ | H | H | H | H | H | 2 or 4 | 177–179[1] | " |
| 27 | H |  | CH$_3$ | H | H | 4-Cl | H | 1, 2 or 4 | | " |

-continued

| Ex. | R₁ | R₂ | R₃ | R₄ | R₅ | R₆ | R₇ | Analogous to Example | M.P. °C. | Centrifugation |
|---|---|---|---|---|---|---|---|---|---|---|
| 28 | H | —CH₂—⌬ (cyclohexyl) | H | H | H | 4-Cl | 6-Cl | 1, 2 or 4 | | " |
| 29 | CH₃ | —CH₂—◁ | H | H | 4-Cl | 4-Cl | H | 1, 2 or 3 | | cis |
| 30 | H | —CH₂—☐ | H | H | H | 4-CF₃ | H | 1, 2 or 4 | | trans |
| 31 | H | CH₂—C≡CH | H | 4-NO₂ | H | H | H | 1, 2 or 3 | | cis |

Key to Table

1. Hydrochloride form
2. Naphthalen-1,5-disulphonate form
3. Hydrogen fumarate form
4. NMR (CDCl₃/RT/TMS): δ=8.3 (m,1H), δ=7.2–8.0 (m,11H), δ=6.60 (m,1H), δ=5.90 (m,1H), δ=3.90 (s,2H), δ=3.35 (m,2H), δ=2.25 (s,3H) [s=singlet, m=multiplet]
5. Starting material VI for process (c); m.p. hydrochloride form 140°–142° (from propanol/ether)
6. NMR (CDCl₃/RT/TMS): δ=8.3 (m,1H), δ=6.8–7.9 (m,10H) δ=6.55 (m,1H), δ=5.90 (m,1H), δ=3.90 (s,2H), δ=3.3 (m,2H), δ=2.25 (s,3H) [s=singlet, m=multiplet]
7. Starting material VI for process (c); m.p. 69°–70° (from ethanol).

What is claimed is:

1. Compounds of formula I,

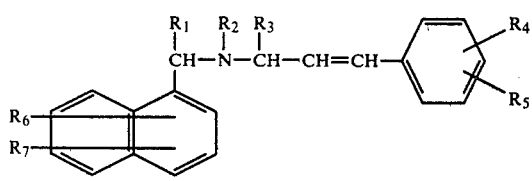

in which
R₁ is hydrogen or alkyl,
R₂ is alkyl, alkenyl, alkynyl, cycloalkyl or cycloalkylalkyl,
R₃ is hydrogen or lower alkyl, and
R₄, R₅, R₆ and R₇, which may be the same or different, each signifies hydrogen, halogen, trifluoromethyl, hydroxy, nitro or lower alkyl or alkoxy, and
chemotherapeutically acceptable acid addition salts thereof.

2. A chemotherapeutic composition comprising a chemotherapeutic effect amount of a compound of claim 1 in association with a chemotherapeutically acceptable diluent or carrier.

3. A method of treating mycotic disorders comprising administering to an animal in need of such treatment, an effective amount of a compound of claim 1.

4. A compound according to claim 1 in which R₂ is alkyl of 1 to 6 carbon atoms.

5. A compound according to claim 4 in which R₁ is hydrogen and R₃ is hydrogen.

6. The compound of claim 1 which is Trans-N-(cinnamyl)-N-methyl-(1-naphthylmethyl)amine.

7. The compound of claim 1 which is Trans-N-[3-(4-fluorophenyl)-2-propenyl]-N-methyl-(1-naphthylmethyl)amine.

8. The compound of claim 1 which is Cis-N-[3-(4-chlorophenyl)-2-propenyl]-N-methyl-1-naphthylmethyl)amine.

9. The compound of claim 1 which is Trans-N-methyl-N-[3-(4-tolyl)-propenyl]-(1-naphthylmethyl)amine.

10. The compound of claim 1 in Trans form in which R₁, R₂, R₃, R₄, R₅, R₆ and R₇ are H, CH₃, H, 4-Cl, H, H and H, respectively.

11. The compound of claim 1 in Trans form in which R₁, R₂, R₃, R₄, R₅, R₆ and R₇ are H, CH₃, H, 4-Cl, 3-Cl, H and H, respectively.

12. The compound of claim 1 in Trans form in which R₁, R₂, R₃, R₄, R₅, R₆ and R₇ are H, CH₃, H, 4-OCH₃, H, H and H, respectively.

13. The compound of claim 1 in Trans form in which R₁, R₂, R₃, R₄, R₅, R₆ and R₇ are H, CH₃, H, H, H, 2-OH and H, respectively.

14. The compound of claim 1 in Trans form in which R₁, R₂, R₃, R₄, R₅, R₆ and R₇ are H, CH(CH₃)₂, H, H, H, H and H, respectively.

15. The compound of claim 1 in Trans form in which R₁, R₂, R₃, R₄, R₅, R₆ and R₇ are H, CH₃, H, H, H, 2-CH₃ and H, respectively.

16. The compound of claim 1 in Trans form in which R₁, R₂, R₃, R₄, R₅, R₆ and R₇ are CH₃, CH₃, H, H, H, H and H, respectively.

17. The compound of claim 1 in Trans form in which R₁, R₂, R₃, R₄, R₅, R₆ and R₇ are H, CH₃, H, 2-F, H, H and H, respectively.

18. The compound of claim 1 in Trans form in which R₁, R₂, R₃, R₄, R₅, R₆ and R₇ are H, CH₃, H, 2—Cl, H, H and H, respectively.

19. The compound of claim 1 in Trans form in which R₁, R₂, R₃, R₄, R₅, R₆ and R₇ are H, CH₃, H, 4—OH, H, H and H, respectively.

20. The compound of claim 1 in Trans form in which R₁, R₂, R₃, R₄, R₅, R₆ and R₇ are H, C₂H₅, H, H, H, H and H, respectively.

21. The compound of claim 1 in Trans form in which R₁, R₂, R₃, R₄, R₅, R₆ and R₇ are H, CH₃, H, H, H, 4—Cl and H, respectively.

22. The compound of claim 1 in Trans form in which R₁, R₂, R₃, R₄, R₅, R₆ and R₇ are H, CH₃, H, H, H, 4—CH₃ and H, respectively.

23. The compound of claim 1 in Trans form in which R₁, R₂, R₃, R₄, R₅, R₆ and R₇ are H, CH₃, H, H, H, 2—OCH₃ and H, respectively.

24. The compound of claim 1 in Trans form in which R₁, R₂, R₃, R₄, R₅, R₆ and R₇ are H, CH₃, H, H, H, 4—OCH₃ and H, respectively.

25. The compound of claim 1 in Cis form in which R₁, R₂, R₃, R₄, R₅, R₆ and R₇ are H, CH₃, H, H, H, H and H, respectively.

26. The compound of claim 1 in Cis form in which $R_1$, $R_2$, $R_3$, $R_4$, $R_5$, $R_6$ and $R_7$ are H, $CH_3$, H, 4-F, H, H and H, respectively.

27. The compound of claim 1 in Trans form in which $R_1$, $R_2$, $R_3$, $R_4$, $R_5$, $R_6$ and $R_7$ are H, $CH_2$—$CH$=$CH_2$, H, H, H, H and H, respectively.

28. A pharmaceutical composition according to claim 2 in which the compound is Trans-N-cinnamyl-N-methyl(1-naphthylmethyl)amine.

29. A method according to claim 3 in which the compound is Trans-N-cinnamyl-N-methyl-(1-naphthylmethyl)amine.

* * * * *

UNITED STATES PATENT AND TRADEMARK OFFICE

CERTIFICATE EXTENDING PATENT TERM
UNDER 35 U.S.C. 156

Patent No.    : 4,282,251

Dated         : August 4, 1981

Inventor(s)   : Daniel Berney

Patent Owner  : Sandoz Pharmaceuticals Corporation

This is to certify that there has been presented to the

COMMISSIONER OF PATENTS AND TRADEMARKS an application under 35 U.S.C. 156 for an extension of the patent term. Since it appears that the requirements of law have been met, this certificate extends the term of the patent for the period of

2 YEARS with all rights pertaining thereto as provided by 35 USC 156(b).

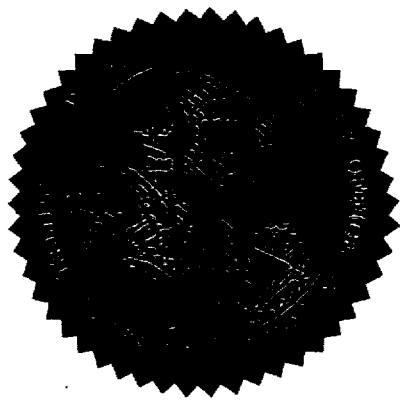

I have caused the seal of the Patent and Trademark Office to be affixed this Twenty-Third day of February 1989.

Donald J. Quigg

Assistant Secretary and Commissioner of Patents and Trademarks